| United States Patent [19] | [11] Patent Number: 4,777,320 |
| Alvila et al. | [45] Date of Patent: Oct. 11, 1988 |

[54] TWO STEP PROCESS FOR PRODUCING ISOBUTYLENE FROM PROPYLENE AND SYTHESIS GAS

[75] Inventors: Leila Alvila; Tapani Pakkanen, both of Joensuu; Outi Krause; Matteus Joutsimo, both of Helsinki, all of Finland

[73] Assignee: Neste Oy, Finland

[21] Appl. No.: 27,163

[22] Filed: Mar. 17, 1987

[30] Foreign Application Priority Data

Mar. 18, 1986 [FI] Finland ................. 86 1133

[51] Int. Cl.⁴ .................. C07C 1/24; C07C 29/16
[52] U.S. Cl. ...................... 585/139; 568/909
[58] Field of Search ............... 568/909; 585/639, 640

[56] References Cited

U.S. PATENT DOCUMENTS

| | | |
|---|---|---|
| 2,660,433 | 5/1953 | Mallan et al. ............ 585/639 |
| 2,818,440 | 12/1957 | Rust et al. ............ 585/639 |
| 3,342,879 | 9/1967 | Pine ............ 585/639 |
| 3,780,127 | 12/1973 | Young et al. ............ 585/639 |
| 4,144,191 | 3/1979 | Hartwell et al. ............ 568/883 |
| 4,234,752 | 11/1980 | Wu et al. ............ 585/640 |
| 4,602,119 | 7/1986 | Drake ............ 585/639 |

*Primary Examiner*—J. E. Evans
*Attorney, Agent, or Firm*—Steinberg & Raskin

[57] ABSTRACT

A two step process for producing isobutylene from propylene and synthesis gas. In the first step, propylene is contacted with synthesis gas at elevated temperature in the presence of a catalyst system containing a mixture of monometal compounds $M_4(CO)_{12}$ and $M'_4(CO)_{12}$ and/or bimetal compound $M_2M'_2(CO)_{12}$ where M and M' are different metals of the cobalt group. The alcohol mixture thus-obtained is dehydrated in the second step, to produce a product fraction containing a large amount of isobutylene.

4 Claims, No Drawings

TWO STEP PROCESS FOR PRODUCING ISOBUTYLENE FROM PROPYLENE AND SYTHESIS GAS

BACKGROUND OF THE INVENTION

The present invention concerns a two step process for producing isobutylene from propylene and synthesis gas.

$C_4$-olefines have been used as starting materials for numerous petrochemical industrial processes. The greatest part of the total quantity of isobutylene and n-butylene is consumed in producing petrol components in so-called catalytic polymerizing or alkylation. However, both isobutylene and n-butylenes are being used ever more often as starting materials for various chemical compounds. Traditionally, butylene rubbers and polyisobutylene have been made from isobutylene. The demand for the compound has considerably increased in recent years, along with that for methylisobutylene ether (MTBE). The starting materials in the production of MTBE, which is an agent improving the octane number of petrol in great demand, are isobutylene and methanol. The demand for isobutylalcohol (TBA) has also increased for the same reason as that for MTBE. TBA is obtained from isobutylene upon hydration. Isobutylene is further consumed, for instance, in the manufacturing of tertiary butylphenols and butylcresols. of methylmethacrylate.

$C_4$-olefines are principally commercially produced by two different standard procedures: floating catalytic cracking (FCC), and steam cracking. In the first-noted process, petrol components are produced by cracking heavier crude oil fractions. In this connection, liquid petroleum gas fractions are formed as by-products, among others. Ethylene is the product in the latter process. In addition to the manufacturing as cracking products, it is possible to produce butylenes by dehydrogenating the equivalent paraffins. Dehydrogenation processes are expensive, with one of the essential limiting factors being the availability of the starting materials, above all that for isobutylene.

SUMMARY OF THE INVENTION

Accordingly, it is an object of the present invention to provide a new and improved manner of synthesizing isobutylene.

It is also an object of the present invention to facilitate the ease of synthesizing isobutylene, e.g. in just two steps.

It is another object of the present invention to provide for greater selectivity in the synthesis of isobutylene.

These and other objects are attained by the present invention which offers a new, advantageous procedure for producing isobutylene in which $C_3$-olefines, in particular propylenes, can be used as starting materials.

In the procedure of the invention for producing isobutylene, propylene is contacted in a first step with synthesis gas at elevated temperature and in the presence of a catalyst system containing a mixture of the monometal cluster compounds $M_4(CO)_{12}$ and $M_4'(CO)_{12}$ and/or a bimetal compound $M_2 M_2' (CO)_{12}$ where M and M' are different metals of the cobalt group (in the Periodic Table of the Elements), after which the alcohol mixture thus obtained is dehydrated in a second step in order to produce a product fraction containing a great deal of isobutylene.

This new manner of producing $C_4$-olefines thus uses $C_3$-olefines for starting material. The process involves synthesis in two steps or stages: in the first step, propylene is hydroformylated to become a mixture of n-butanol and isobutanol; and in the second step, the alcohols that have been obtained in the first step are dehydrated to become olefines:

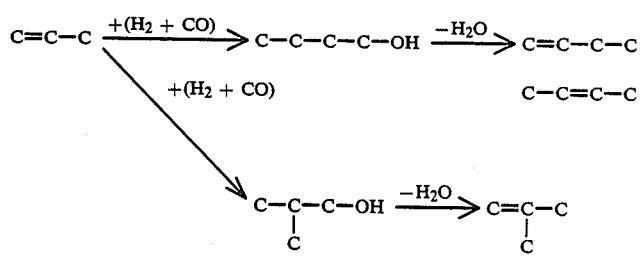

DESCRIPTION OF THE PREFERRED EMBODIMENTS

In conventional hydroformylation processes, homogeneous cobalt or rhodium compounds serve as the catalyst. One of the most important objects in developing these processes, has been the highest possible selectivity of compounds with straight chains. It should be noted that the most important products were n-butanol and 2-ethylhexanol, while in the present invention isobutanol is desired. The best and most active catalyst for producing n-butanol has turned out to be ligand-modified rhodium carbonyl. With this catalyst, aldehydes are almost exclusively formed (selectivity is typically 96%), while the proportion of straight-chained: branched is 10–14:1 (Catalysts in $C_1$ Chemistry, ed. W. Keim, 1983). If it is desired to form olefines from from the aldehydes which have been produced, it then becomes necessary first to hydrogenate the aldehydes to produce the equivalent alcohols. Modified cobalt catalysts produce alcohols (selectivity 80%). The hydrogenating capacity thereof is so good that alkanes are formed with about 15% selectivity.

In the isobutylene producing process of the present invention, the newest catalysts are utilized, with which it is possible to directly obtain alcohols by hydroformylation, the selectivity of alcohol formation being 95%. Such catalysts have been described in Finnish patent application No. 84 4634 and in U.S. Pat. No. 4,144,191. The proportion of straight-chain: branched products obtained with these new catalyst, varies over the range of about 1.1:1 to about 1.3:1. Thus, the proportion of straight-chain: branched products is also different from those obtained with commercial products, i.e., the proportion of the iso form is considerably higher. Since in the developing of commercial hydroformylation processes, maximum selectivity in favor of straight-chain fractions was important while the result of hydroformylation mainly resulted in aldehydes which had to be hydrogenated in order obtain an alcohol, it has not been previously possible to selectively produce in two steps, a product fraction with a high isobutylene content by applying commercial catalysts.

In the process of the present invention, cluster compounds formed by rhodium and cobalt serve as catalysts, in which the ligands are typically carbonyl groups. These cluster compounds may be either monometallic, such as $Co_4(CO)_2$ and $Rh_4(CO)_{12}$, or bimetallic, such as $Rh_2Co_2(CO)_{12}$. The preparation of these catalysts has been described in the patent and application cited above. The hydroformylation processing conditions are typically total pressure about 20-55 bar, hydrogen/carbon monoxide proportion about 1:1, and temperature about 50°-200° C.

In hydroformylation, utilizing the above-mentioned catalyst, alcohol mixtures are obtained which contain about 50% n-butanol and about 50% isobutanol.

Decomposing alcohols to olefines by dehydrating is a process known in the art. This process is catalyzed by acids. Typical catalysts include activated aluminum oxide, phosphoric acid on a carrier, zinc oxide on aluminum oxide carrier, and clay, aluminum silicate, zeolites or ion exchange resins.

The processing conditions applied depend upon the catalysts and starting materials. Tertiary alcohols, for instance, are dehydrated with considerably greater ease than primary and secondary alcohols. Conditions also have an effect on selectivity. In addition to olefines, ethers are also produced from alcohols, especially at the lowest temperatures, particularly from those alcohols having a straight chain. It is possible that n-butanol alone is converted to butylenes. In that case, a 5A molecular sieve constitutes the catalyst. Isobutanol will then fail to react and can be used, for instance, as a solvent or as a petrol component.

When carrying out dehydration with aluminum oxide catalyst, the temperature must be typically kept over 300° C. in order for the formation of ethers to be minimized.

The present invention will be further described with reference to the following examples:

EXAMPLE 1

A catalyst for use in the hydroformylation reaction was prepared by mixing together 30 mg of a monometal compound compound $Co_4(CO)_{12}$; 57 mg of a monometal compound $RH_4(CO)_{12}$ and 125 mg aminic ion exchange resin Dowex MWA-P, and 10 ml toluene, which was mixed for 18 hours in nitrogen atmosphere. The toluene, containing unbound clusters, was removed, with the catalyst being dried in a vacuum.

Hydroformylation of propylene took place with a 50 bar starting pressure. The partial pressures were: $p_H=20$ bar; $p_{CO}=25$ bar; and $p_C=5$ bar. The temperature was 100° C., the catalyst quantity 100 mg and the reaction time, 17 hours.

The reaction product contained 98.9% butanols and 1.1% aldehydes. Among the alcohols, the proportion of straight-chained: branched alcohols was 1.3:1.

Dehydration of the alcohols was carried out in a continuous-action, solid bed reactor. The catalyst was aluminum oxide (Harshaw Al-3996 R). Processing conditions were: pressure=1 bar, temperature=300° C.; and LHSV=1.5 hours.

Under these conditions, the alcohol conversion was 100%, with the composition of the product obtained therefrom being 33% 1-butylene, 19% 2-butylenes, 48% isobutylene, and 0.3% ethers.

EXAMPLE 2

In the hydroformylation reaction, a catalyst was employed which was the bimetal cluster $Co_2Rh_2(CO)_{12}$ and aminic ion exchange resin MWA-1, with cobalt content 7.9% and rhodium content 13.9%.

Hydroformylation of propylene was carried out with a starting pressure of 55 bar. The partial pressures were: hydrogen 25 bar; carbon monoxide 25 bar; and propylene 5 bar. The temperature was 100° C., the catalyst quantity 50 mg., and the reaction time 17 hours.

The reaction product contained 96% butanols, 3% aldehydes, and 1% miscellaneous. Among the alcohols, the straight chain/branched proportion was 1.15:1.

Dehydration of the alcohols was performed as in Example 1, with the product containing 48% isobutylene.

EXAMPLE 3

In the hydroformylation reaction, a catalyst was employed which was prepared by mixing together 1.0 g aluminum oxide (Alumina grades D, dried at 800° C.) and a cluster compound mixture containing 0.035 g $Co_4(CO)_{12}$ (Strem Chemicals) and 0.071 g $Rh_4(CO)_{12}$ (Martinego, S. et al., Inorganic Synthesis, vol. 20, 1980, p. 209), and 0.020 dm$^3$ hexane, in nitrogen atmosphere for 16 hours. The hexane, containing unbound cluster, was removed. The catalyst was rinsed with hexane and dried in a vacuum.

Propylene hydroformylation was carried out under 54 bar pressure. The partial pressures were: hydrogen 25 bar; carbon monoxide 25 bar; and propylene 4 bar. The catalyst quantity was 350 mg., the temperature 100° C., and the reaction time 17 hours.

The liquid product contained 88% alcohols and 7% aldehydes. Among the butanols, the straight-chain/branched proportion was 1.1:1.

Alcohol dehydration was carried out as in Example 1, with the product containing 48% isobutylene.

The preceding description of the present invention is merely exemplary, and is not intended to limit the scope thereof in any way.

What is claimed is:

1. Method for producing isobutylene from propylene and synthesis gas, comprising
   (1) contacting said propylene with said synthesis gas at a temperature of about 50°-200° C. and at a pressure of about 20-55 bar in the presence of a catalyst comprising a mixture of monometal compounds $M_4(CO)_{12}$ and $M'_4(CO)_{12}$ wherein M and M' are Co and Rh respectively, to produce a mixture of alcohols, and
   (2) then dehydrating the thus-produced alcohol mixture to form a mixture of $C_4$-olefines including isobutylene.

2. The method of claim 1, wherein a portion of straight-chain: branched alcohols formed in the first step is about 1.1:1 to about 1.3:1.

3. The method of claim 1, wherein ratio of $H_2:CO$ in the synthesis gas is about 1:1.

4. Method for producing isobutylene from propylene and synthesis gas, comprising the steps of
   hydroformylating the propylene with the synthesis gas at a temperature of about 50°-200° C. and at a pressure of about 20–55 bar in the presence of a catalyst comprising a mixture of monometal compounds $M_4(CO)_{12}$ and $M'_4(CO)_{12}$ wherein M and M' are cobalt and rhodium respectively, to form a mixture of n-butanol and isobutanol, and
dehydrating the thus-formed n-butanol and isobutanol to form $C_4$-olefines with a high degree of selectivity of isobutylene,
whereby the isobutylene is produced from propylene and synethesis gas in just two steps.

* * * * *